United States Patent [19]

Murakami et al.

[11] 4,013,773
[45] Mar. 22, 1977

[54] SOLID COMPOSITION

[75] Inventors: Masuo Murakami; Hiroitsu Kawada, both of Tokyo; Tadayoshi Ohmura, Higashikurume; Hiroshi Sugiura, Tokyo, all of Japan

[73] Assignee: Yamanouchi Pharmaceutical Co., Ltd., Tokyo, Japan

[22] Filed: Feb. 4, 1975

[21] Appl. No.: 547,022

Related U.S. Application Data

[63] Continuation-in-part of Ser. No. 312,972, Dec. 7, 1972, abandoned.

[30] Foreign Application Priority Data

Dec. 9, 1971  Japan .............................. 46-99676

[52] U.S. Cl. .............................. 424/284; 252/315; 252/316; 252/DIG. 1; 424/311; 426/650; 426/651
[51] Int. Cl.² ................ A61K 31/355; A61K 31/22
[58] Field of Search ........... 252/316, 315; 424/308, 424/284, 311

[56] References Cited

UNITED STATES PATENTS

| | | | |
|---|---|---|---|
| 2,940,900 | 6/1960 | Benton, Jr. et al. | 424/284 |
| 3,553,148 | 1/1971 | Bourland | 252/316 |
| 3,708,514 | 1/1973 | Murakami et al. | 424/308 X |

FOREIGN PATENTS OR APPLICATIONS

| | | | |
|---|---|---|---|
| 727,645 | 4/1955 | United Kingdom | 252/316 |

*Primary Examiner*—Richard D. Lovering
*Attorney, Agent, or Firm*—Burgess Ryan and Wayne

[57] ABSTRACT

A single phase solid composition wherein one part of a non-aqueous liquid and 0.5–6 parts of calcium lactate hydrate are mixed and heated. The product according to this invention is very stable and can be formed into various kinds of moldings by a simple operation so that it may be applied to many uses.

2 Claims, No Drawings

SOLID COMPOSITION

This is a continuation of application Ser. No. 312,972, filed Dec. 7, 1972, and now abandoned.

DETAILED EXPLANATION OF INVENTION

This invention relates to a new solid composition. More particularly, it relates to a single phase solid composition wherein one part of non-aqueous liquid and 0.5–6 parts of a calcium lactate hydrate are mixed and heated.

The solid composition according to this invention, though it is formed by solidifying a non-aqueous liquid, is very stable and can be formed into various kinds of moldings by a simple operation so that it may be applied to many uses.

The solid composition in the form of particle according to this invention shows such a good fluidity that it may be preferable to use as powder, granules, pills, tablets and capsules. Those products in the form of a mass of gypsum-like material are suitable to use, for example, as a solid fuel in which an oil as fuel is solidified, a solid flavour material in which a liquid flavour is solidified, and the like.

Previously, since non-aqueous liquids were difficult to weigh, divide into packages, and were generally inconvenient to handle, it has been desired eagerly to solidify such materials.

At the time of this application, there has been employed for the solidification of a non-aqueous liquid, a method involving adsorbing such a material on an excipient such as starch, lactose, microcrystalline cellulose, anhydrous silicic acid, calcium citrate, synthetic aluminum silicate, magnesium oxide, etc.

However, due to the insufficient adsorption capacity of these excipients, the non-aqueous liquid is solidified apparently but is sticky and unstable and the once adsorbed liquid may spread out when the amount of excipient is not sufficient with respect to the non-aqueous liquid. Further, it is not even solidified with starch or lactose. Therefore, for the solidification of a non-aqueous liquid, a large amount of excipient should be used. Finally, only a small amount of liquid may be present with respect to the amount of excipient, so that the volume of end product is disadvantageously very large with respect to the amount of liquid required. Moreover, while the solidification of said liquid by using such a large amount of excipient may provide a solid in the form of powder, the resulting product does not have sufficient fluidity resulting in difficulty in weighing, dividing in packages as well as the inconvenience in handling.

Moreover, since anhydrous silicic acid, synthetic aluminum silicate and microcrystalline cellulose have a large specific volume and are fluffy, not only is the handling of the product inconvenient but the solid material in the form of a powder, which is obtained by using a large amount of excipient with respect to said liquid, has disadvantageously the same property as the excipient itself, i.e. it has a rather large specific volume and is fluffy. Additionally, while starch, lactose, magnesium oxide and calcium citrate have a relatively small specific volume, such material must be used in an especially very large amount for the solidification in the formation of a powder resulting in disadvantageously, an extremely large volume as mentioned above.

As is obviously seen from the above description, while various methods for the solidification of a non-aqueous liquid have been known at the time of this application, there has not been known a method in which said liquid is converted into a stable solid composition using an excipient of a small specific volume in a relatively small amount with respect to said liquid.

As a result of a detailed study of the method for the solidification of non-aqueous liquid disclosed in the art, it has been found that a single phase solid composition obtained by mixing one part of one or more than two parts of non-aqueous liquids with 0.5–6 parts of calcium lactate hydrate having a small specific volume and heating the mixture is very stable and the resulting product can be formed into various kinds of moldings by a very simple operation and applied to many uses.

The adsorption of said non-aqueous liquid by calcium lactate has never known and it is quite unexpected that the mixing and heating of said components provides a very stable solid composition which can be easily formed into various kinds of moldings.

As regards the non-aqueous liquids which can be used in this invention, there are included compounds other than water, which are liquid such as wax or materials which are viscous semi-fluids at ordinary temperature, such as, for example: vitamin A, vitamin E acetate, linoleic acid, liver oil, methyl linoleate, ethyl α-(p-chlorophenoxy)iso-butyrate (common name: clofibrate), dimethyl polysiloxane, castor oil, soybean oil, peppermint oil, cinnamon oil, camellia oil, olive oil, eucalyptus oil, maize oil, oleic acid, liquid paraffin, polyethylene glycol, propylene glycol, nonyl phenyl polyoxyethylene ether, dialkyl benzyl ammonium halide, dodecyl polyaminoethyl glycine, kerosene, flavour oil, glycerine, silicone oil, octyl decyl triglyceride, and the like.

As for the calcium lactate hydrate which can be used for the preparation of said solid composition according to this invention, in general, calcium lactate pentahydrate is used.

For the preparation of said solid composition according to this invention, one part of a non-aqueous liquid and 0.5–6, preferably 1–3 parts of calcium lactate hydrate are mixed homogeneously and illustratively by means of a mortar, mixer etc. and the resulting cream thus obtained is heated at above 40° C, preferably from 60°–150° C for from 5 min. to about 1 hour generally in a thermostat drier etc.

The solid composition thus obtained is quite different from the cream before the heating and a solid composition in the form of mass.

In the preparation of said solid composition according to this invention, said non-aqueous liquid and calcium lactate hydrate are dissolved or suspended in water or a low-boiling solvent, which is volatilized on heating, such as acetone or alcohol by means of a homogenizer etc. and then dried by heating to yield a glossy gypsum-like solid composition.

The mass or gypsum-like solid composition which is obtained as mentioned above can be changed to the solid composition in the form of particles by grinding with a pulverizer, etc.

Further, in the preparation of said solid composition according to this invention, when said non-aqueous liquid and calcium lactate hydrate are dissolved or suspended in water or a low-boiling solvent, which is volatilized on heating, such as acetone or alcohol by means of a homogenizer etc. and then heated and spray-dried, the solid composition in the form of particles is obtained at once.

In the mixing of said non-aqueous liquid with calcium lactate hydrate, additives such as a coloring agent, tasting agent, perfuming agent, diluent, etc. may be added, if desired, and a mixture of more than two kinds of liquids may be used for the preparation of solid composition.

The nature of the solid composition in the form of particle according to this invention using one part of clofibrate as said non-aqueous liquid is compared with compositions obtained by the known method in the following Table I:

TABLE I

| Excipient Name | Amount (part) | Nature of Composition | Note |
| --- | --- | --- | --- |
| Corn Starch | 1.5 | Muddy cream in the form of slurry and no fluidity | Known |
| Microcrystalline cellulose | 1.5 | Sticky funicular wet powder | " |
| Silicic anhydrate | 1.5 | sticky pendular powder 1) | " |
| Calcium lactate pentahydrate | 1.5 | well-fluid powder (free from wetting and sticky property) | According to this invention |
| Corn starch | 6 | Sticky fluid-free funicular wet powder | Known |
| Microcrystalline cellulose | 6 | sticky pendular powder 1) | " |
| Silicic anhydrate | 6 | less-fluid bulky fluffy powder 2) | " |
| Calcium lactate pentahydrate | 6 | well-fluid powder (free from wetting and sticky property) | According to this invention |

1) a little fluidity
2) free from wetting and sticky property.

As is obviously seen from the above table, when the amount of excipient is 1.5 or 6 parts, the solid composition according to this invention containing calcium lactate as an excipient is free from difficulties and is suitable for use whereas the compositions obtained by the known method have many undesirable properties rendering them of little or no use commercially, as a practical matter.

EXAMPLE 1

50g Of calcium lactate pentahydrate and 50g of vitamin E acetate are mixed at room temperature to yield a sticky cream. The mixture is heated at 80°-100° C for 30 min. in a thermostat drier to yield a solid composition. The solid composition is ground to form sticky-free fluid granules.

EXAMPLE 2

50g Of calcium lactate pentahydrate and 50g of ethyl α-(p-chlorophenoxy)iso-butyrate (common name: clofibrate) are mixed at room temperature to yield a sticky cream. The mixture is heated at 80°-100° C for 30 min. in a thermostat drier to yield a solid composition.

EXAMPLE 3

75g Of calcium lactate pentahydrate and 50g of castor oil are mixed at room temperature to yield a sticky cream. The mixture is heated at 80°-100° C for 30 min. in a thermostat drier to yield a solid composition.

EXAMPLE 4

100g Of calcium lactate pentahydrate and 50g of soybean oil are mixed at room temperature to yield a sticky cream. The mixture is heated at 60° C and 5 mmHg for 20 min. in a vacuum drier to yield a solid composition.

EXAMPLE 5

500g Of calcium lactate pentahydrate and 250g of polyethylene glycol (400) are mixed at room temperature to yield a sticky cream. The mixture is heated at 80°-100° C for 30 min. in a thermostat drier to yield a solid composition.

EXAMPLE 6

200g of calcium lactate pentahydrate and 200g of ethylene glycol are mixed at room temperature to yield a sticky cream. The mixture is heated at 80°-100° C for 30 min. in a high frequency drier to yield a solid composition.

EXAMPLE 7

50g Of calcium lactate pentahydrate and 25g of alkyl betaine (Anion BF) are mixed at room temperature to yield a sticky cream. The mixture is heated at 80°-100° C for 30 min. in a thermostat drier to yield a solid composition.

EXAMPLE 8

100g Of calcium lactate pentahydrate and 100g of alkyl dimethyl benzalconium chloride (Cation $F_2$-50) are mixed at room temperature to yield a sticky cream. The mixture is heated at 80°-100° C for 30 min. in a thermostat drier to yield a solid composition.

EXAMPLE 9

50g Of calcium lactate pentahydrate and 50g of polyoxyethylene nonyl phenyl ether (Nikkol SO-15) are mixed at room temperature to yield a sticky cream. The mixture is heated at 80°-100° C for 30 min. in a thermostat drier to yield a solid composition.

EXAMPLE 10

50g Of calcium lactate pentahydrate and 25g of sorbitan sesquioleate are mixed at room temperature to yield a sticky cream. The mixture is heated at 80°-100° C for 30 min. in a thermostat drier to yield a solid composition.

EXAMPLE 11

100g Of calcium lactate pentahydrate and 100g of glycerine are mixed at room temperature to yield a sticky cream. The mixture is heated at 80°-100° C for 30 min. in a thermostat drier to yield a solid composition.

EXAMPLE 12

100g Of calcium lactate pentahydrate, 50g of fluid paraffin and 25g of alkyl betanine (Anion BF) are mixed at room temperature to yield a sticky cream. The mixture is heated at 80°-100° C for 30 min. in a thermostat drier to yield a solid composition.

EXAMPLE 13

100g of calcium lactate pentahydrate, 50g of vitamin E acetate and 10g of isopropyl alcohol are mixed at room temperature to yield a sticky cream. The mixture is heated at 70° C for 10 min. in a heating device to yield a solid composition.

EXAMPLE 14

70g Of calcium lactate pentahydrate are dissolved in 50g of hot water at 80°–100° C, 2g of sucrose fatty acid ester (S-770) is added at 80°–100° C and stirred by means of homogenizer, 100g of vitamin E acetate are then added at 80°–100° C. and stirred by means of homogenizer to emulsify the mixture. Then, on spray-drying in a conventional manner, a solid composition in the form of particles is obtained.

EXAMPLE 15

50g Of calcium lactate pentahydrate, 50g of clofibrate and 1g of polyoxyl stearate (40) are emulsified in 250ml of purified water as described in Example 14 and subjected to a conventional spray-drying treatment to yield a solid composition, in the form of particles.

EXAMPLE 16

70g Of calcium lactate pentahydrate are dissolved in 50g of hot water at 80°–100° C, 100g of polyethylene glycol (400) are added at 80°–100° C and stirred by means of homogenizer and the temperature of the mass is lowered to room temperature to yield a glossy gypsum-like white solid.

EXAMPLE 17

300g Of calcium lactate pentahydrate and 50g of clofibrate are mixed at room temperature and the resulting mixture is heated at 80°–100° C for 10 min. in a thermostat drier to yield a solid composition.

What is claimed is:
1. A single phase solid composition consisting of one part of Vitamin E acetate and 0.5–6 parts of calcium lactate hydrate.
2. A single phase solid composition consisting of 1 part of clofibrate and 0.5–6 parts of calcium lactate hydrate.

* * * * *

UNITED STATES PATENT OFFICE
CERTIFICATE OF CORRECTION

Patent No. 4,013,773                     Dated March 22, 1977

Inventor(s)   Masuo Murakami, et al

It is certified that error appears in the above-identified patent and that said Letters Patent are hereby corrected as shown below:

Column 1, line 10: After "of" insert --a--.

Column 3, Table I: Change "and no fluidity Sticky funicular wet powder" to --Sticky and no fluidity funicular wet powder--.

Column 3, Table I: The first item under "Known" should be a ditto mark; delete the dash.

Signed and Sealed this twelfth Day of July 1977

[SEAL]

Attest:

RUTH C. MASON
*Attesting Officer*

C. MARSHALL DANN
*Commissioner of Patents and Trademarks*